United States Patent
Breuil et al.

(10) Patent No.: US 9,050,590 B2
(45) Date of Patent: Jun. 9, 2015

(54) CATALYTIC COMPOSITION AND PROCESS FOR OLIGOMERIZATION OF OLEFINS USING SAID CATALYTIC COMPOSITION

(71) Applicant: IFP ENERGIES NOUVELLES, Rueil-Malmaison Cedex (FR)

(72) Inventors: Pierre Alain Breuil, Lyons (FR); Adrien Boudier, Lyons (FR)

(73) Assignee: IFP ENERGIES NOUVELLES, Rueil-Malmaison Cedex (FR)

( * ) Notice: Subject to any disclaimer, the term of this patent is extended or adjusted under 35 U.S.C. 154(b) by 232 days.

(21) Appl. No.: 13/762,789

(22) Filed: Feb. 8, 2013

(65) Prior Publication Data

US 2013/0211168 A1 Aug. 15, 2013

(30) Foreign Application Priority Data

Feb. 10, 2012 (FR) ..................... 12 00398

(51) Int. Cl.
| | |
|---|---|
| C07C 2/30 | (2006.01) |
| B01J 31/22 | (2006.01) |
| B01J 31/12 | (2006.01) |
| C08F 4/60 | (2006.01) |
| B01J 31/02 | (2006.01) |
| B01J 31/14 | (2006.01) |
| B01J 31/18 | (2006.01) |
| C07C 2/32 | (2006.01) |
| C08F 10/00 | (2006.01) |
| C08F 110/02 | (2006.01) |

(52) U.S. Cl.
CPC .............. *B01J 31/2295* (2013.01); *C07C 2/30* (2013.01); *B01J 31/0202* (2013.01); *B01J 31/0237* (2013.01); *B01J 31/0238* (2013.01); *B01J 31/143* (2013.01); *B01J 31/1815* (2013.01); *B01J 31/183* (2013.01); *C07C 2/32* (2013.01); *B01J 2531/0238* (2013.01); *B01J 2531/842* (2013.01); *B01J 2531/845* (2013.01); *C07C 2531/18* (2013.01); *C07C 2531/22* (2013.01); *C08F 110/02* (2013.01); *C08F 10/00* (2013.01)

(58) Field of Classification Search
None
See application file for complete search history.

(56) References Cited

U.S. PATENT DOCUMENTS

| | | | |
|---|---|---|---|
| 2009/0209713 A1 | 8/2009 | McGuiness et al. | |
| 2011/0009581 A1* | 1/2011 | Rangheard et al. | ........... 526/172 |
| 2013/0018214 A1 | 1/2013 | Zheng et al. | |

FOREIGN PATENT DOCUMENTS

| | | |
|---|---|---|
| WO | 00/64906 A1 | 11/2000 |
| WO | 2007/039851 A2 | 4/2007 |
| WO | 2011/120336 A1 | 10/2011 |

OTHER PUBLICATIONS

Search Report for FR 1200398 (Dec. 14, 2012).
B.L. Small et al. "Highly Active Iron and Cobalt Catalysts for the Polymerization of Ethylene", J. Am. Chem. Soc., vol. 120, No. 16 (1998) XP-000669622—pp. 4049-4050.
B.L. Small et al., "Iron-Based Catalysts with Exceptionally High Activities and Selectivities for Oligomerization of Ethylene to Linear α-Olefins", J. Am. Chem. Soc., vol. 120, No. 28 (1998) XP-002086898—pp. 7143-7144.
Database WPI Week 201169—Thomson Scientific, London, GB; AN 2011-M61821—XP-002689055.
A. Boudier et al., "Novel Catalytic System for Ethylene Oligomerization: An Iron (III) Complex with an Anionic N,N,N Ligand", Organometallics, vol. 30, No. 10 (May 23, 2011) pp. 2640-2642.

* cited by examiner

*Primary Examiner* — Yun Qian
(74) *Attorney, Agent, or Firm* — Millen, White, Zelano & Branigan, P.C.

(57) ABSTRACT

The invention relates to a catalytic composition that comprises at least one precursor of iron or cobalt, at least one organic ligand, and an activating agent that consists of at least one derivative of aluminum and at least one organic compound having at least one alcohol group and/or at least one amine group, and in which the molar ratio between the aluminum and the alcohol and/or amine group number present in said organic compound of said activating agent is preferably greater than or equal to 1. The invention also relates to a process for oligomerization of olefins using said catalytic composition.

8 Claims, No Drawings

CATALYTIC COMPOSITION AND PROCESS FOR OLIGOMERIZATION OF OLEFINS USING SAID CATALYTIC COMPOSITION

This invention relates to a catalytic composition and a process for oligomerization of olefins using said catalytic composition.

PRIOR ART

It is known to prepare catalytic compositions for oligomerization of olefins such as ethylene, propylene, butenes, or pentenes. These catalytic compositions comprise in particular a complex of iron and a Lewis acid making it possible to activate the catalyst. By way of examples, the catalytic compositions that are formed by an iron complex comprising a bis(imino)pyridine ligand and an aluminum derivative, generally methylaluminoxane (MAO) prepared by controlled hydrolysis of trimethylaluminum or modified methylaluminoxane (MMAO), make it possible to obtain, in a very selective manner, linear alpha-olefins after oligomerization of ethylene (U.S. Pat. No. 6,417,305 B2). It has also been shown that the nitrogen-containing ligands of alpha-diimine type can—in the presence of iron—lead to active systems for oligomerization of ethylene in the presence of MMAO (U.S. Pat. No. 7,271,121 B2, U.S. Pat. No. 7,727,926 B2) as well as the nitrogen-containing ligands obtained by reaction of a pyridine-type compound substituted with a ketone group with a compound of the family of amino-quinolines (FR 2929944 A1).

In a general manner, these catalytic compositions use an activator that is MAO or one of its derivatives, for example MMAO. These compounds are tailor-made by different producers; there therefore exist significant disparities between the different available MAO in terms of structures, aluminum content, and therefore reactivity in the reactions for oligomerization of olefins. They are difficult to synthesize and to manipulate; these are sensitive compounds, breaking down over short periods of time and having very variable purities. In addition, it is known to one skilled in the art that only the MAO and its derivatives make it possible to obtain catalytic compositions that are very active in oligomerization of olefins.

The MAO-type activating agents therefore have a certain number of drawbacks. The object of this invention is to propose a catalytic composition for oligomerization of olefins not requiring an MAO-type activator.

It has now been found, in an unexpected way, that a catalytic composition that comprises at least one precursor of iron or cobalt, at least one organic ligand, and an activating agent that consists of at least one aluminum derivative and at least one organic compound that has at least one alcohol group and/or at least one amine group, and optionally another additional activating agent, with or without the presence of a solvent, has an activity for the oligomerization of olefins, in particular the oligomerization of ethylene.

The activating agent that replaces the MAO-type activator therefore consists of the derivative of aluminum and the organic compound having at least one alcohol group and/or at least one amine group. Said activating agent preferably has a molar ratio between the aluminum and the alcohol and/or amine group number present in said organic compound that is greater than or equal to 1.

DETAILED DESCRIPTION

Catalytic Composition

The invention relates to a catalytic composition that comprises at least one precursor of iron or cobalt, at least one organic ligand, and an activating agent that consists of at least one derivative of aluminum and at least one organic compound that has at least one alcohol group and/or at least one amine group, and in which the molar ratio between the aluminum and the alcohol and/or amine group number present in said organic compound is preferably greater than or equal to 1.

The precursor of iron or cobalt is a compound of iron or cobalt that may or may not be hydrated and that can contain an anionic, monoanionic, or dianionic group, for example a halide such as a chloride, a fluoride, a bromide or an iodide; a hydrocarbon group, for example a methyl, a benzyl or a phenyl; a carboxylate, for example an acetate, an acetylacetonate, an octoate, an oxalate, a tartrate, an ethyl hexanoate, a lactate, a gluconate or a fumarate; an oxide; an amide, for example a diethyl amide; an alkoxide, for example a methoxide, an ethoxide or a phenoxide; a hydroxide; a nitrate; a sulfate; a pyrophosphate; a phosphate or a perchlorate. Alternatively, the compound of iron or cobalt can contain an anion that is non-coordinating or slightly coordinating, for example a tetrafluoroborate, a p-toluenesulfonate, a trifluoroacetylacetonate, a fluorinated aryl borate or a triflate. The compound of iron or cobalt can also contain a cyclopentadienyl dicarbonyl. The precursors of iron or cobalt may or may not be coordinated with a ligand.

By way of examples, the iron precursor can be selected from among iron(II) chloride, tetrahydrated iron(II) chloride, hexahydrated iron(III) chloride, the iron(II) chloride tetrahydrofuran complex, the iron(II) chloride bis(pyridine) complex, iron(III) chloride, iron(II) fluoride, iron(III) fluoride, iron(II) bromide, iron(III) bromide, iron(II) iodide, iron(III) iodide, iron(II) acetate, iron(III) acetate, iron(II) acetylacetonate, iron(III) acetylacetonate, iron(II) octoate, iron(III) octoate, iron(II) 2-ethylhexanoate, iron(III) 2-ethylhexanoate, iron(II) triflate, iron(III) triflate, iron(III) nitrate, iron(II) sulfate, iron(III) sulfate, iron(II) tartrate, iron(II) oxalate, iron(II) lactate, iron(II) gluconate, iron(II) tetrafluoroborate, iron(II) fumarate, iron(III) pyrophosphate, iron(II) perchlorate, iron(III) perchlorate, iron(III) phosphate, iron(II) p-toluenesulfonate, iron(III) p-toluenesulfonate, iron(III) trifluoroacetylacetonate, and iron(II) cyclopentadienyl dicarbonyl. The iron precursors may or may not be hydrated.

By way of examples, the cobalt precursor can be selected from among cobalt(II) chloride, cobalt(III) chloride, cobalt(II) fluoride, cobalt(III) fluoride, cobalt(II) bromide, cobalt(III) bromide, cobalt(II) iodide, cobalt(III) iodide, cobalt(II) acetate, cobalt(III) acetate, cobalt(II) acetylacetonate, cobalt(III) acetylacetonate, cobalt(II) octoate, cobalt(III) octoate, cobalt(II) 2-ethylhexanoate, cobalt(III) 2-ethylhexanoate, cobalt(II) triflate, cobalt(III) triflate, cobalt(III) nitrate, cobalt(II) sulfate, cobalt(III) sulfate, cobalt(II) tartrate, cobalt(II) oxalate, cobalt(II) lactate, cobalt(II) gluconate, cobalt(II) tetrafluoroborate, cobalt(II) fumarate, cobalt(III) pyrophosphate, cobalt(II) perchlorate, cobalt(III) perchlorate, cobalt(III) phosphate, cobalt(II) p-toluenesulfonate, cobalt(III) p-toluenesulfonate, cobalt(III) trifluoroacetylacetonate, and cobalt(II) cyclopentadienyl dicarbonyl. The cobalt precursors may or may not be hydrated.

The organic ligand of said catalytic composition according to the invention comprises at least one heteroatom that is selected from among nitrogen, oxygen, phosphorus and/or sulfur.

By way of examples, the ligand optionally can be selected from among the bis(imino)pyridine compounds, the alpha-diimine compounds having a group that may or may not be donors, the phenanthroline compounds, the phenoxyimine compounds, the oxazoline compounds, the iminopyridine compounds, the aminopyridine compounds, the imidazole compounds, and the carbenic compounds, which may or may not be functionalized.
By way of non-limiting examples, the ligand can be selected from among the compounds that have as a general formula:
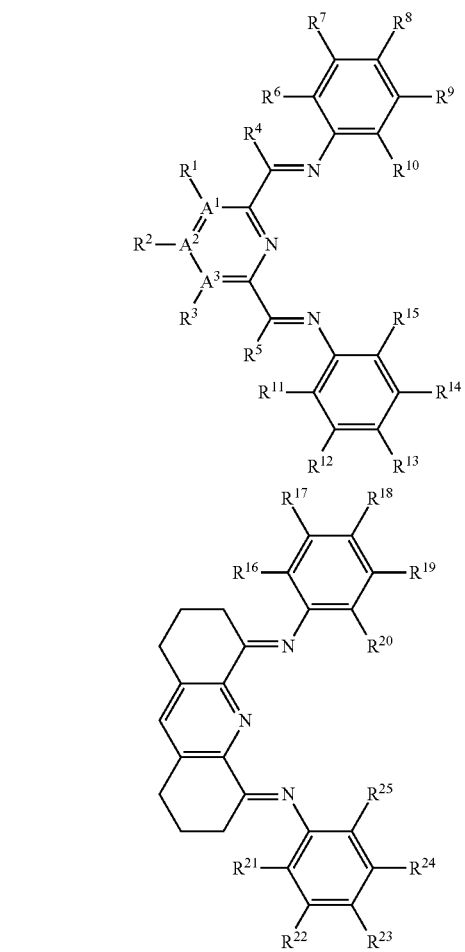
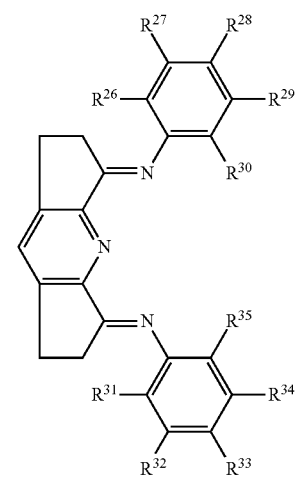
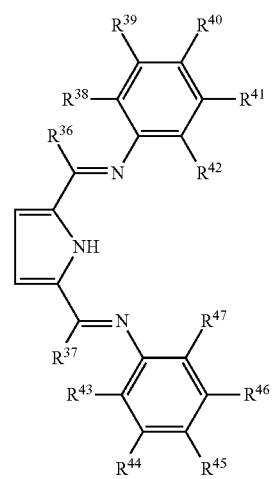
-continued
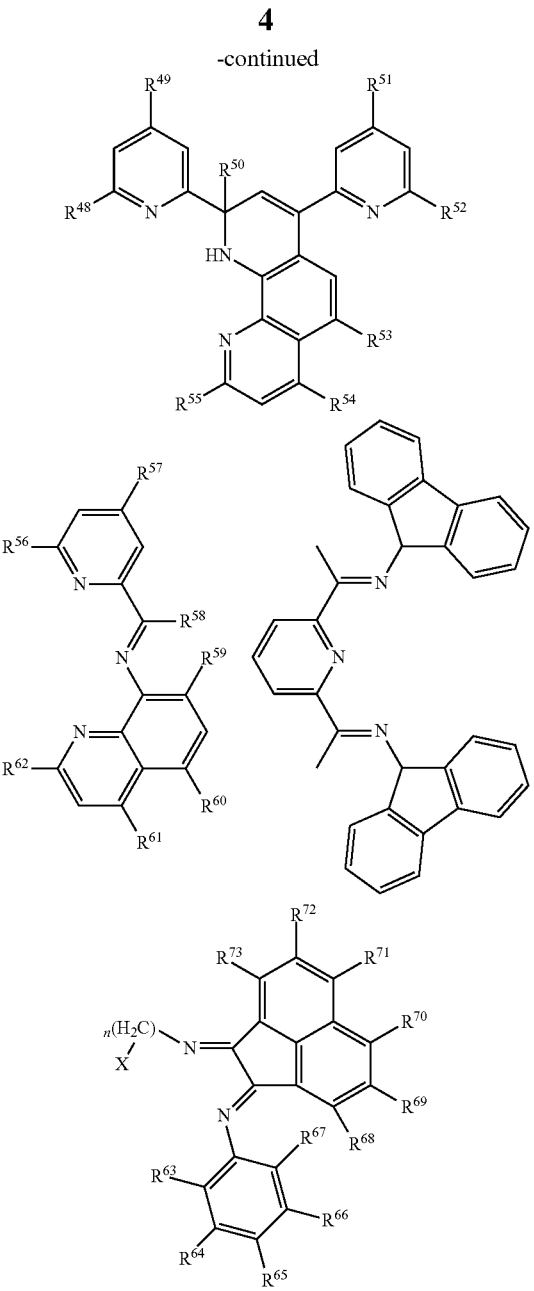
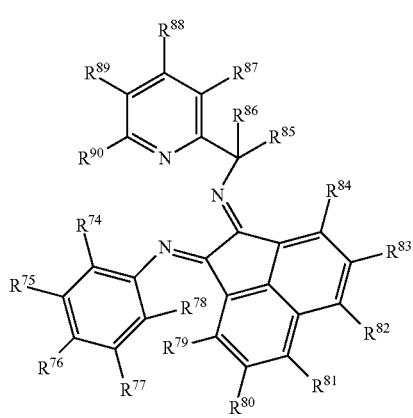

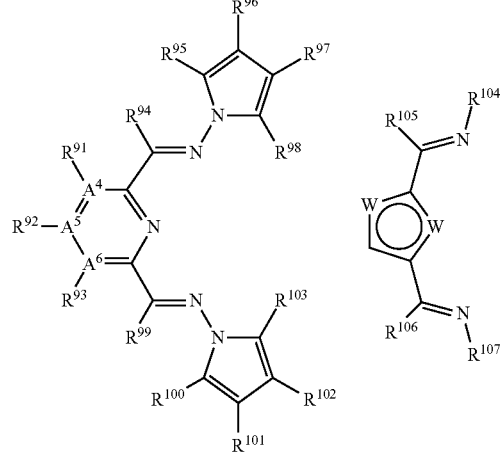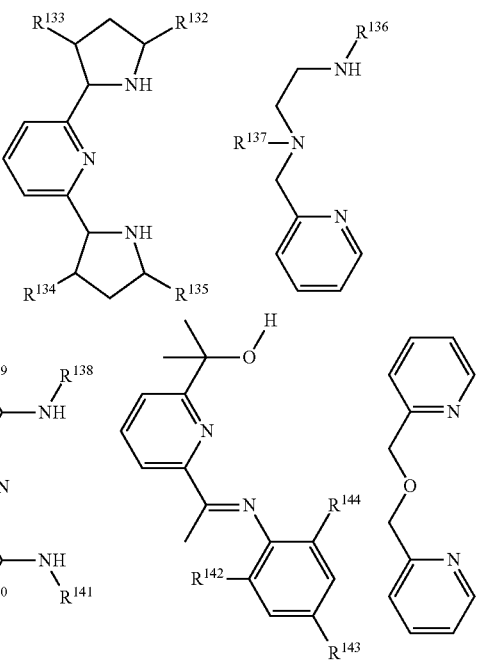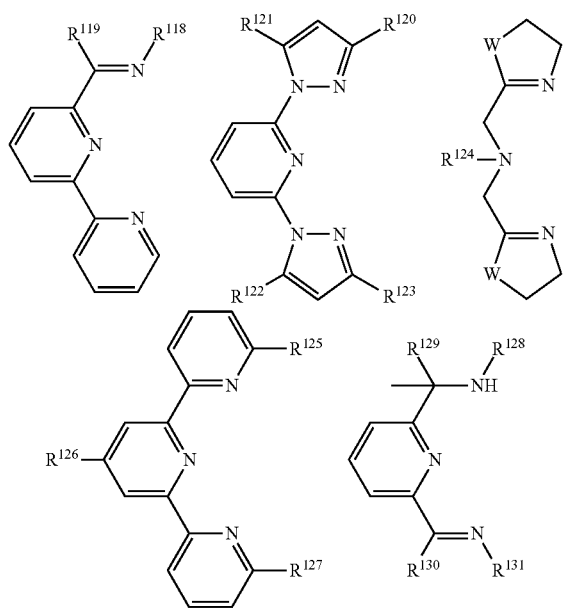

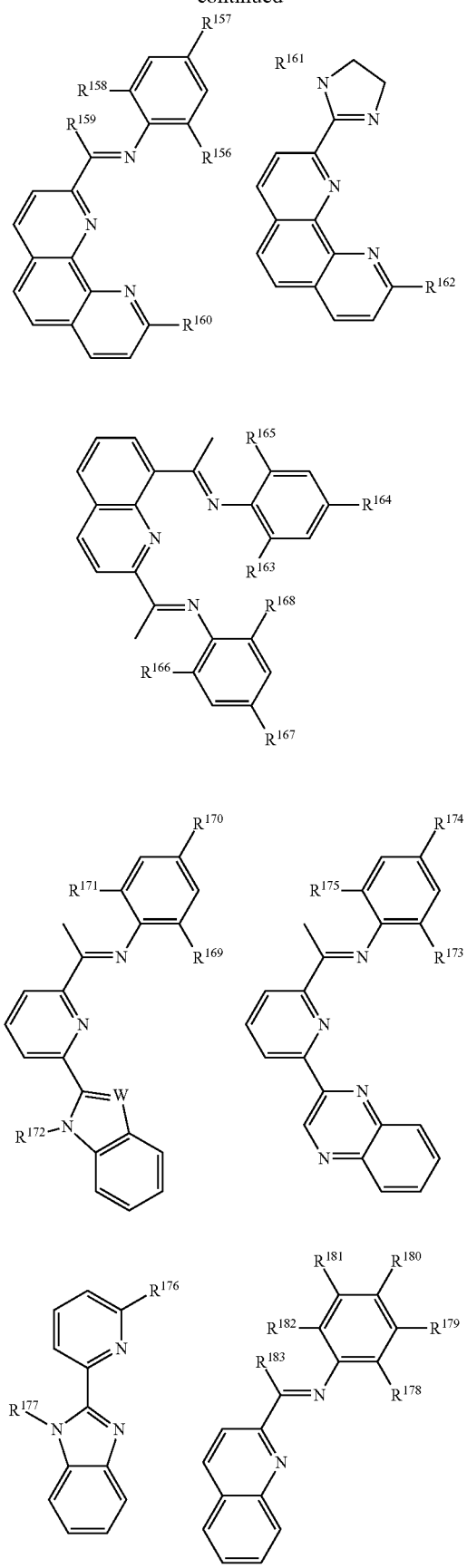
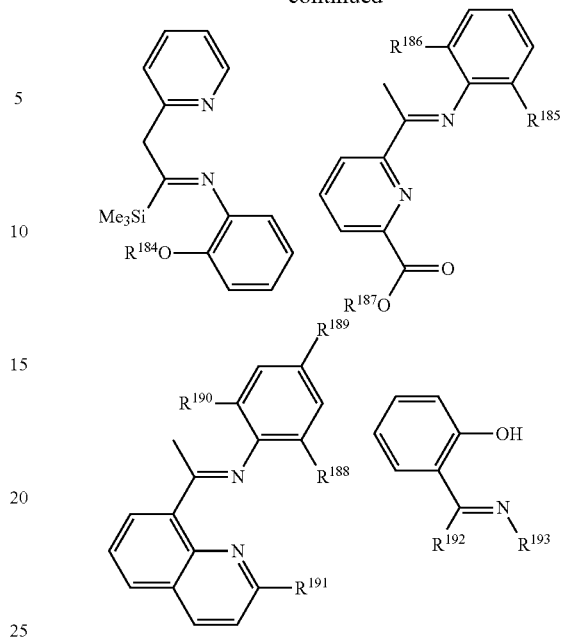

where the groups $R^1$ to $R^{193}$ can be identical or different, are selected from among the hydrogen atom, the linear or branched alkyl groups, which may or may not be cyclic, saturated or unsaturated, the aryl, aralkyl or alkaryl groups comprising 1 to 12 carbon atoms, the groups containing heteroelements, which may be heterocyclic or not, aromatic or not, halides or not, or with or without substrate, and preferably selected from among the alkoxyl group, the nitro group, the halide group and/or the perfluoroalkyl group; where $A^1$ to $A^6$ can be identical or different, are selected from among the atoms of carbon or nitrogen;

where n is a whole number of between 1 and 4, W is an atom or a group having a heteroatom, preferably W is selected from among oxygen, sulfur or NH, X is a group that has a heteroatom, preferably X is selected from among the groups $OR^{194}$, $SR^{195}$, or $P(R^{196}R^{197})$, $R^{194}$ to $R^{197}$ can be identical or different and are selected from among the hydrogen atom, the linear or branched alkyl groups that may or may not be cyclic, saturated or unsaturated, the aryl, aralkyl or alkaryl groups comprising 1 to 12 carbon atoms, the groups containing heteroelements, which may be heterocyclic or not, aromatic or not, halides or not, with or without substrate, and preferably selected from among the alkoxy group, the nitro group, the halide group and/or the perfluoroalkyl group.

By way of nonlimiting examples, the groups $R^1$ to $R^{197}$ can be selected from among the following groups: hydrogen, methyl, ethyl, isopropyl, iso-butyl, tert-butyl, cyclohexyl, phenyl, benzyl, methoxy, nitro, dimethylamine, diethylamine, diisopropylamine, trifluoromethyl, fluoride, chloride, bromide and iodide.

The activating agent consists of at least one aluminum derivative and at least one organic compound that has at least one alcohol group and/or at least one amine group. The definition of the organic compound is understood to exclude the carboxylic acids or water.

The aluminum derivative of said catalytic composition according to the invention is preferably selected from among the tris(hydrocarbyl)aluminums and/or the hydrocarbylaluminum halide compounds. As examples of the aluminum derivatives, the following can be included: the alkylaluminums, such as, for example, trimethylaluminum, triethylaluminum, tributylaluminum, triisobutylaluminum, trihexylaluminum, tri-n-octylaluminum, isoprenylaluminum, or the alkylaluminum hydrides, such as, for example, diisobutylaluminum hydride; or else the alkylaluminum halides, such as, for example, dimethylaluminum chloride, diethylaluminum chloride, ethylaluminum dichloride, methylaluminum sesquichloride, ethylaluminum sesquichloride, methylaluminum dichloride, and isobutylaluminum dichloride, used by themselves or in a mixture.

The organic compound that has at least one alcohol group and/or at least one amine group of said catalytic composition according to the invention is preferably selected from among the aliphatic, cyclic or aromatic compounds, which may or may not be substituted, containing additional heteroelements or not, and taken by themselves or in a mixture.

In a preferred manner, the organic group that has at least one alcohol group and/or at least one amine group can be selected from among the aliphatic, cyclic or aromatic alcohols, the aliphatic, cyclic or aromatic amines, the aliphatic, cyclic or aromatic amino alcohols, whereby said compounds can be substituted or not, containing additional heteroelements or not, or taken by themselves or in a mixture.

In a preferred manner, the organic compound is selected from among methanol, ethanol, n-propanol, i-propanol, n-butanol, i-butanol, t-butanol, pentanols, hexanols, heptanols, octanols, nonanols, decanols, cyclopentanol, cyclohexanol, phenol, 2-hydroxytoluene, 3-hydroxytoluene, 4-hydroxytoluene, 2,6-dimethylphenol, 3,5-dimethylphenol, 2,3,4,5,6-pentamethylphenol, 2-chlorophenol, 3-chlorophenol, 4-chlorophenol, 2,3,4,5,6-pentachlorophenol, 2-iodophenol, 3-iodophenol, 4-iodophenol, 2,3,4,5,6-pentaiodophenol, 2-fluorophenol, 3-fluorophenol, 4-fluorophenol, 2,3,4,5,6-pentafluorophenol, 3,5-trifluoromethylphenol, 2-bromophenol, 3-bromophenol, 4-bromophenol, 2,3,4,5,6-pentabromophenol, 2-tert-butylphenol, 3-tert-butylphenol, 4-tert-butylphenol, 2,6-di-tert-butylphenol, 3,5-di-tert-butylphenol, 2,6-di-tert-butyl-4-methylphenol, 3-phenylphenol, 4-phenylphenol, 2,6-diphenylphenol, 2,4,6-triphenylphenol, methylamine, ethylamine, n-propylamine, i-propylamine, n-butylamine, i-butylamine, t-butylamine, ethanolamine, 3-aminopropanol, 4-aminobutanol, 2-aminophenol, and 3-aminophenol.

The organic compounds that have several alcohol groups and/or several amine groups can be selected from among the aliphatic, cyclic or aromatic polyols that contain at least two alcohol groups, the aliphatic, cyclic or aromatic polyamines that contain at least two amine groups, or else amino alcohols, with said compounds being able to be substituted or not, containing additional heteroelements or not, taken by themselves or in a mixture.

In a preferred manner, the organic compound is selected from among 1,2-ethanediol, 1,2-propanediol, 1,3-propanediol, 2,2-dimethylpropane-1,3-diol, 1,4-butanediol, 2,3-dimethylbutane-2,3-diol, cis-2-butene-1,4-diol, 1,2-ethanediamine, 1,2-propanediamine, 1,3-propanediamine, 2,2-dimethylpropane-1,3-diamine, 1,4-butanediamine, 2,3-dimethylbutane-2,3-diamine, cis-2-butene-1,4-diamine, benzopinacol, 1,5-pentanediol, 2,2-dimethylpentane-1,3-diol, 2,4-dimethylpentane-2,4-diol, 1,6-hexanediol, 2,5-dimethylhexane-2,5-diol, 1,2-dihydroxybenzene, 1,3-dihydroxybenzene, 1,4-dihydroxybenzene, 1,2-dihydroxy-4-tert-butylbenzene, 2,3-dihydroxy-biphenyl, 1,2,3-benzenetriol, 1,2,4-benzenetriol, 1,3,5-benzenetriol, 2,3-naphthalenediol, 1,2-naphthalenediol, 1,5-pentanediamine, 2,2-dimethylpentane-1,3-diamine, 2,4-dimethylpentane-2,4-diamine, 1,6-hexanediamine, 2,5-dimethylhexane-2,5-diamine, 1,2-diaminobenzene, 1,3-diaminobenzene, 1,4-diaminobenzene, 1,2-diamino-4-tert-butylbenzene, 2,3-diamino-biphenyl, 1,2,3-benzenetriamine, 1,2,4-benzentriamine, 1,3,5-benzenetriamine, 2,3-naphthalenediamine, 1,2-naphthalenediamine, 1,2,3,4,5,6-benzenehexyl, glycerol, trimethylolpropane, 1,6-hexanediol, 1,2,6-hexanetriol, 1,6-hexanediamine, 1,2,6-hexanetriamine, sucrose, glucose, sorbitol, pentaerythrol, mannitol, triethanolamine, N-methyl diethanolamine or the compounds that are described by the following formulas:

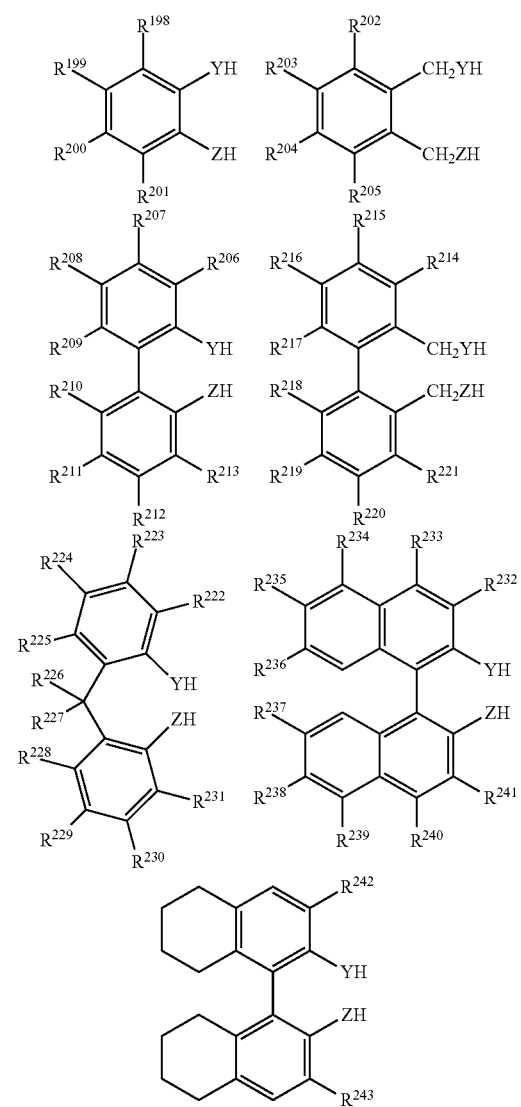

where $R^{198}$ to $R^{243}$ can be identical or different, are selected from among the hydrogen atom, the linear or branched alkyl groups, which may or may not be cyclic, saturated or unsaturated, the aryl, aralkyl or alkaryl groups comprising 1 to 12 carbon atoms, the groups containing heteroelements, which may be heterocyclic or not, aromatic or not, halides or not, or with or without substrate, and preferably selected from among the alkoxy group, the nitro group, the halide group and/or the perfluoroalkyl group; where Y and Z can be identical or different and can be an oxygen atom or an NH group.

By way of nonlimiting examples, the groups $R^{198}$ to $R^{243}$ can be selected from among the following groups: hydrogen, methyl, ethyl, iso-propyl, iso-butyl, tert-butyl, cyclohexyl, phenyl, benzyl, methoxy, nitro, dimethylamine, diethylamine, diisopropylamine, trifluoromethyl, fluoride, chloride, bromide and iodide.

An additional activating agent can optionally be added to said catalytic composition, although this is not necessary. The activating agent that is used in this invention is preferably a Lewis acid. In a preferred manner, the Lewis acid is selected from among the derivatives of aluminum and the derivatives of boron or zinc or a mixture of these derivatives. As examples of the aluminum derivatives, there can be included: the alkylaluminums, such as, for example, trimethylaluminum, triethylaluminum, tributylaluminum, triisobutylaluminum, trihexylaluminum, tri-n-octylaluminum, isoprenylaluminum, or alkylaluminum hydrides, such as, for example, diisobutylaluminum hydride; or else alkylaluminum halides, such as, for example, dimethylaluminum chloride, diethylaluminum chloride, ethylaluminum dichloride, methylaluminum sesquichloride, ethylaluminum sesquichloride, methylaluminum dichloride, isobutylaluminum dichloride, and aluminoxanes, used by themselves or in a mixture. The aluminoxanes are well known by one skilled in the art as oligomeric compounds that can be prepared by the controlled addition of water on an alkylaluminum, for example trimethylaluminum. Such compounds can be linear, cyclic or mixtures of these compounds. They are generally represented by the formula $[RAlO]_a$, where R is a hydrocarbon group and a is a number from 2 to 50. Preferably, the aluminoxane is selected from among methylaluminoxane (MAO) and/or ethylaluminoxane (EAO) and/or from among the modified aluminoxanes such as modified methylaluminoxane (MMAO).

As examples of boron derivatives, the following can be included: trialkylboranes, such as, for example, trimethylborane, triethylborane, tripropylborane, tri-n-butylborane, triisobutylborane, tri-n-hexylborane, tri-n-octylborane, used by itself or in a mixture; tris(aryl)boranes, such as, for example, tris(perfluorophenyl)borane, tris(3,5-bis(trifluoromethyl)phenyl)borane, tris(2,3,4,6-tetrafluorophenyl)borane, tris(perfluoronaphthyl)borane, tris(perfluobiphenyl)borane and derivatives thereof. It is also possible to use as activator the (aryl)borates associated with a triphenylcarbenium cation or with a trisubstituted ammonium cation such as triphenylcarbenium tetrakis(perfluorophenyl)borate, N,N-dimethylanilinium tetrakis(perfluorophenyl)borate, N,N-diethylanilinium tetrakis(3,5-bis(trifluoromethyl)phenyl)borate, or triphenylcarbenium tetrakis(3,5-bis(trifluoromethyl)phenyl)borate. As examples of zinc derivatives, the following can be included: dialkylzincs, such as, for example, dimethylzinc, diethylzinc, dipropylzinc, dibutylzinc, dineopentylzinc, di(trimethylsilylmethyl)zinc, used by itself or in a mixture.

Said iron or cobalt precursor of the catalytic composition according to the invention can be mixed with said ligand of the catalytic composition according to the invention with or without the presence of a solvent, called a preparation solvent. An iron or cobalt complex optionally can be obtained by mixing said iron or cobalt precursor with said ligand of the catalytic composition according to the invention according to any preparation process known to one skilled in the art.

Said preparation solvent can advantageously be identical to or different from the reaction solvent, i.e., the solvent that is used for the oligomerization process according to the invention. Said solvents (for preparation and reaction) are advantageously selected from among the organic solvents and preferably from among ethers, alcohols, chlorinated solvents and hydrocarbons that are saturated, unsaturated, aromatic or not, and cyclic or not. Preferably, said solvents are selected from among hexane, cyclohexane, heptane, butane or isobutane, monoolefins or diolefins preferably comprising 4 to 20 carbon atoms, benzene, toluene, orthoxylene, mesitylene, ethylbenzene, dichloromethane, chlorobenzene, in pure form or in a mixture, or else a mixture of olefins produced by an oligomerization process, preferably the olefin mixture produced by the oligomerization process using the catalytic composition and/or ionic liquids. Said solvents can be used by themselves or in a mixture. In the case where said solvents are an ionic liquid, they are advantageously selected from among the ionic liquids described in the patents U.S. Pat. No. 6,951,831 B2 and FR 2895406 B1.

Said iron or cobalt complex can be obtained by the preparation process comprising an oxidation stage that is described in the patent FR 2926029 or by the preparation process comprising the use of a base described in the patent FR 2937262.

Said iron or cobalt complex of the catalytic composition that may or may not be diluted in said preparation solvent can advantageously be used directly in the oligomerization process according to the invention.

Said iron or cobalt complex of the catalytic composition can also advantageously be isolated and then used, dilute or not, in a solvent, in the oligomerization process according to the invention.

Said aluminum derivative of the catalytic composition according to the invention can be mixed with said organic compound having at least one alcohol group and/or an amine group of the catalytic composition according to the invention with or without the presence of a solvent, called a preparation solvent according to the invention, at a temperature of between −100° C. and 100° C. Said mixture of the aluminum derivative and the organic compound having at least one alcohol group and/or one amine group of the catalytic composition according to the invention is advantageously prepared according to any preparation process known to one skilled in the art. Said preparation solvent can advantageously be identical to or different from the reaction solvent, i.e., the solvent that is used for the oligomerization process according to the invention. Said solvent for preparation of the activating agent can advantageously be identical to or different from the solvent for preparation of the iron or cobalt complex.

Said mixture of the aluminum derivative and the organic compound having at least one alcohol group and/or one amine group of the catalytic composition that may or may not be diluted in said preparation solvent can advantageously be used directly in the oligomerization process according to the invention.

Said mixture of the aluminum derivative and the organic compound having at least one alcohol group and/or one amine group of the catalytic composition can also advantageously be isolated and then used, diluted or not, in a solvent in the oligomerization process according to the invention.

Said catalytic composition according to the invention can also advantageously be prepared in situ in the reaction section and in the solvent that is used for the oligomerization process according to the invention. In this case, the mixing order of the iron or cobalt precursor, the ligand, the aluminum derivative and the organic compound having at least one alcohol group and/or one amine group is not critical. An additional activating agent can also be added.

The molar ratio between the ligand and the iron or cobalt precursor is advantageously between 0.05 and 10, preferably between 0.5 and 2, and preferably 1.

The molar ratio between aluminum and the iron or cobalt complex is advantageously between 1/1 and 1,000/1, and preferably between 1/1 and 500/1.

The molar ratio between aluminum and the alcohol and/or amine group number present in said organic compound is preferably greater than or equal to 1. There is therefore preferably at least one aluminum atom per alcohol and/or amine group. The ratio is advantageously between 100/1 and 1/1, and preferably between 10/1 and 1/1.

Oligomerization Reaction

Another object of this invention relates to a process for oligomerization of olefins comprising 2 to 10 carbon atoms using said catalytic composition. Preferably, said process is a process for oligomerization of ethylene. The oligomerization is defined as the transformation of a monomer unit into a compound or mixture of compounds of general formula $C_pH_{2p}$ with $4 \leq p \leq 80$, preferably with $4 \leq p \leq 50$, in a preferred manner with $4 \leq p \leq 26$, and in a more preferred manner with $4 \leq p \leq 14$.

The olefins that are used in the oligomerization process according to the invention are olefins that comprise 2 to 10 carbon atoms, and preferably said olefins are selected from among ethylene, propylene, butene-1 and pentene-1, by themselves or in a mixture, in pure or dilute form. In the case where said olefins are diluted, said olefins are diluted by one or more alkane(s), such as are found in "fractions" obtained from petroleum refining processes, such as catalytic cracking or steam-cracking. In a preferred manner, the olefin that is used in the oligomerization process according to the invention is ethylene.

Said olefins can come from non-fossil resources such as biomass. For example, the olefins that are used in the oligomerization process according to the invention can advantageously be produced from alcohols, and in particular by dehydration of alcohols. In one preferred embodiment, said olefins are produced by dehydration of ethanol for producing ethylene.

The oligomerization process according to the invention and preferably the process for oligomerization of ethylene advantageously operates at a total pressure of between atmospheric pressure and 20 MPa, preferably between 0.5 and 8 MPa, and at a temperature of between −40 and +250° C., preferably between 0° C. and 150° C. The concentration of iron or cobalt in the catalytic solution is advantageously between $1.10^{-5}$ and 1 mol/L, and preferably between $5.10^{-5}$ and $1.10^{-2}$ mol/L.

The heat generated by the reaction can advantageously be eliminated by all of the means that are known to one skilled in the art.

The oligomerization process according to the invention and preferably the process for oligomerization of ethylene can advantageously be conducted in a closed system, a semi-open system or continuously, with one or more reaction stages. Vigorous stirring is advantageously implemented to ensure good contact between the reagent(s) and the catalytic composition.

The oligomerization process according to the invention and preferably the process for oligomerization of ethylene can advantageously be implemented intermittently. In this case, a selected volume of the solution comprising the catalytic composition according to the invention is introduced into a reactor that is equipped with common devices for stirring, heating and cooling. The ethylene pressure and the temperature are adjusted to the desired values. The pressure within the reactor is kept constant by introducing ethylene until the total volume of liquid that is produced represents, for example, 2 to 50 times the volume of the solution comprising the catalytic composition originally introduced. The catalytic composition is destroyed by any common means known to one skilled in the art, and then the products are drawn off and separated from the solvent.

The oligomerization process according to the invention and preferably the process for oligomerization of ethylene can also advantageously be implemented continuously. In this case, the solution comprising the catalytic composition according to the invention is injected at the same time as the ethylene into a reactor that is stirred by the conventional mechanical means or by external recirculation, and kept at the desired temperature. In another embodiment, the components of said catalytic composition can also be injected in a separate manner, for example the organic compound having at least one alcohol group and/or one amine group and the aluminum derivative, on the one hand, and the iron or cobalt precursor and the ligand, on the other hand. Ethylene is introduced by a pressure-controlled intake valve that keeps the ethylene constant. The reaction mixture is drawn off by means of a valve controlled at the liquid level in such a way as to keep the mixture constant. The catalytic composition is continuously destroyed by any common means known to one skilled in the art, and then the products of the reaction as well as the solvent are separated, for example by distillation. The olefin that has not been transformed can be recycled in the reactor.

The oligomerization process according to the invention and preferably the process for oligomerization of ethylene can advantageously be implemented in a reactor with one or more reaction stages in series, with the olefinic feedstock and/or the catalytic composition that is pre-conditioned in advance or the different components of said catalytic composition being introduced continuously, either in the first stage, or in the first stage and any other of the stages. At the outlet of the reactor, the catalytic composition can be deactivated, for example by injection of ammonia and/or an aqueous solution of soda and/or an aqueous solution of sulfuric acid. The unconverted olefins and the alkanes that are optionally present in the feedstock are next separated from the oligomers by distillation.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 12/00.398, filed Feb. 10, 2012 are incorporated by reference herein.

EXAMPLES

The following examples illustrate the invention without limiting its scope.

Preparation of Iron Complex 1:

The iron complex is prepared in the following way: the bis(imino)pyridine ligand (1.58 g; 1.05 equivalents) and the tetrahydrated iron(II) dichloride precursor (0.88 g; 1 equivalent) are added in a Schlenk line under argon containing a bar magnet. 150 ml of THF is then added, and the solution is stirred at ambient temperature for 16 hours. The solid that is formed is isolated by filtration and then washed with ether and pentane (2.17 g; 91%).

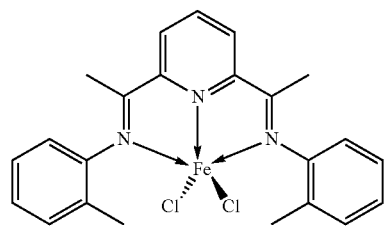

Iron Complex 1

Preparation of Iron Complex 2:

The iron complex is prepared in the following way: the ligand 1,2-dihydro-1,10-phenantroline (0.374 g; 1 equivalent) is deprotonated by n-BuLi (0.068 g; 1 equivalent) in 20 ml of THF at −78° C. in a Schlenk line under argon containing a bar magnet. The anhydrous iron(III) trichloride precursor (0.174 g/l equivalent) in 10 ml of THF is next added to the reaction medium. The solution is stirred under cold conditions for 1 hour, and then at ambient temperature for 16 hours. The solid that is formed is isolated by filtration and then washed with diethyl ether and with pentane (0.460 g; 90%).

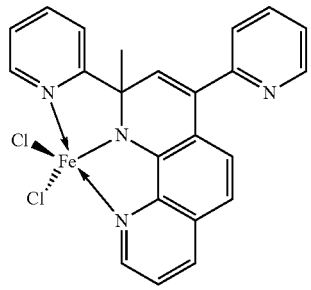

Iron Complex 2

Catalytic Tests: Oligomerization of Ethylene

The catalytic compositions according to the invention containing the iron complex 1 or 2 have been used in the oligomerization of ethylene by varying the nature of the organic compound of the activating agent and the ratio of the organic compound containing the alcohol and/or amine group to aluminum.

The mixture of alcohol and/or amine with the aluminum derivative is prepared in advance in the following manner: the alcohol and/or amine is/are introduced into a Schlenk line to which 15 ml of toluene is added. The medium is cooled to −78° C. The trimethylaluminum (TMA) in toluene (3 ml) is added drop by drop. The reaction medium is stirred for 30 minutes at −78° C. and then is allowed to return to ambient temperature.

The 100-ml reactor is dried under vacuum at 140° C. for 2.5 hours and then is placed under ethylene. The iron complex ($1 \times 10^{-5}$ mol) in 7 ml of toluene is introduced as activating agent into 18 ml of toluene. The feedstock is introduced into the reactor until reaching a pressure of 30 bar. Stirring is started up, and the temperature setting is fixed at 50° C. After the desired reaction time, neutralization is achieved outside of the reactor with aqueous $H_2SO_4$.

TABLE 1

Catalytic Tests Performed with Iron Complex 1 or 2 According to the Procedure Described Above.[a]

| No. | Fe Complex | Organic Compound with Alcohol and/or Amine Group | Organic Compound/AlMe₃ Ratio | m $C_2H_4$ (g) | Time (Minutes) | Oligomerization Activity ($\times 10^5$ $g \cdot mol^{-1} \cdot h^{-1}$) |
|---|---|---|---|---|---|---|
| 1 | 1 | phenol (PhOH) | 1/1 | 5.9 | 60 | 5.9 |
| 2 | 1 | cyclohexanol | 1/1 | 6.7 | 60 | 6.7 |
| 3 | 1 | 4-phenylphenol (Ph-C₆H₄-OH) | 1/1 | 4.6 | 60 | 4.6 |
| 4 | 1 | 2,6-di-tBu-phenol | 1/1 | 3.6 | 60 | 3.6 |
| 5 | 1 | HO-(CH₂)₄-OH | 1/2 | 12.9 | 60 | 12.9 |
| 6 | 1 | 2,2'-biphenol | 1/2 | 25 | 25 | 60.0 |
| 7 | 1 | HO-CH₂CH₂-OH | 1/2 | 2.9 | 60 | 2.9 |
| 8 | 1 | catechol | 1/2 | 22.7 | 60 | 22.7 |

TABLE 1-continued

Catalytic Tests Performed with Iron Complex 1 or 2 According to the Procedure Described Above.[a]

| No. | Fe Complex | Organic Compound with Alcohol and/or Amine Group | Organic Compound/AlMe$_3$ Ratio | m C$_2$H$_4$ (g) | Time (Minutes) | Oligomerization Activity (×10$^5$ g·mol$^{-1}$·h$^{-1}$) |
|---|---|---|---|---|---|---|
| 9 | 1 | 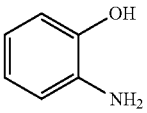 | 1/2 | 11.0 | 60 | 11.0 |
| 10 | 1 | 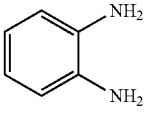 | 1/2 | 11.6 | 60 | 11.6 |
| 11 | 1 | 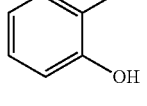 | 1/2 | 4.8 | 60 | 4.8 |
| 12[b] | 1 | 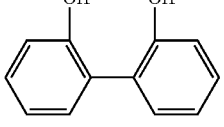 | 1/5 | 23.2 | 60 | 23 |
| 13 | 1 | 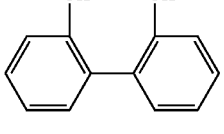 | 1/2 | 23.3 | 24 | 59 |
| 14 | 1 | 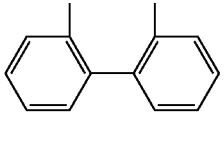 | 2/3 | 25.2 | 8 | 189 |
| 15 | 1 | 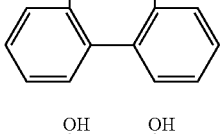 | 4/5 | 15.8 | 60 | 16 |
| 16[c] | 2 | 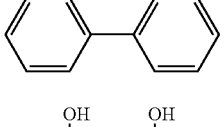 | 2/3 | 4.8 | 60 | 4.8 |
| 17[d] | 1 | 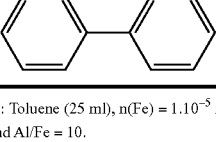 | 2/3 | 15.2 | 60 | 15.2 |

[a]Operating Conditions: Toluene (25 ml), n(Fe) = 1.10$^{-5}$ mol, P = 30 bar, T = 50° C., Al/Fe = 500.
[b]n(Fe) = 0.15 mmol and Al/Fe = 10.
[c]Iron complex 2 used, Al/Fe = 250.
[d]The formation of the mixture of alcohol and/or amine is implemented in situ in the reactor: the corresponding alcohol diluted in the toluene is introduced, and then the trimethylaluminum; the medium is stirred at ambient temperature for 10 minutes. Then, the iron precursor 1 in toluene is injected into the reactor. The feedstock is introduced into the reactor until reaching a pressure of 30 bar. Stirring is started up, and the temperature setting is fixed at 50° C.. After the desired reaction time, neutralization is achieved outside of the reactor with aqueous H$_2$SO$_4$.

By way of indication, the selectivities that are obtained during the test 6, for example, are similar to those obtained with a reference test using MAO (methylaluminoxane). A Schulz-Flory-type oligomer distribution is achieved; the calculated coefficient is 0.67. The alpha-olefin selectivities in the fractions are greater than 99%.

A very good activity of ethylene oligomerization in the case of use of the catalytic compositions according to the invention is observed.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A catalytic composition comprising at least one iron dichloride tetrahydrate, at least one bis(imino)pyridine, and an activating agent consisting of at least one trimethyl aluminum and at least one organic 2,2-biphenol-diol compound.

2. The catalytic composition according to claim 1, in which the molar ratio between aluminum and the 2,2-biphenol-diol compound number present is greater than or equal to 1.

3. The catalytic composition according to claim 1, in which the organic ligand is:

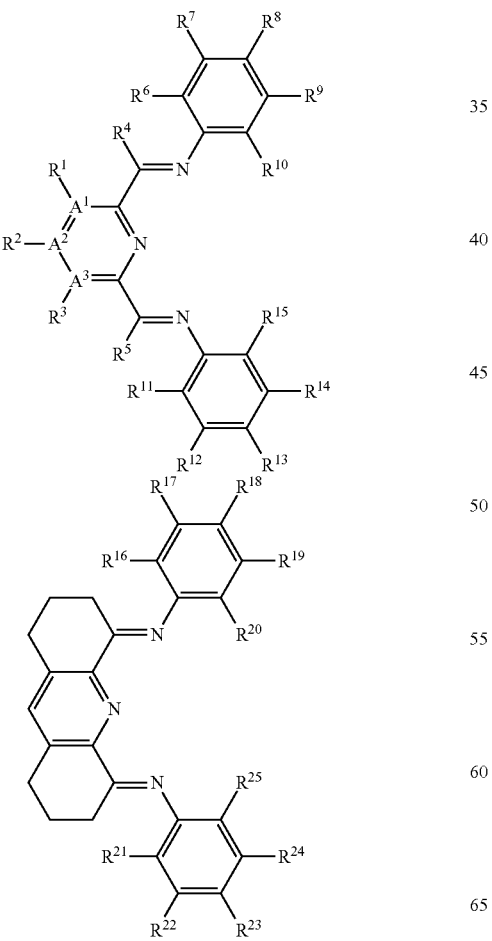

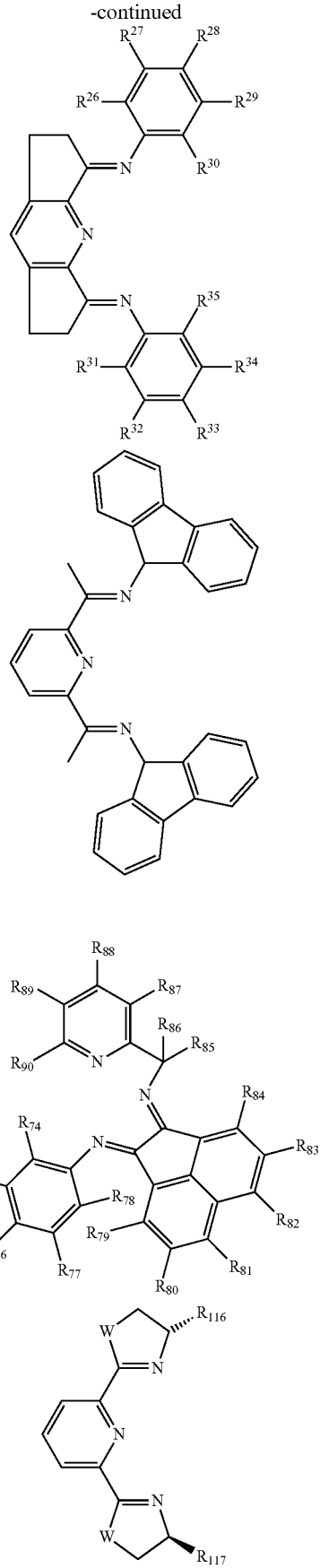

-continued

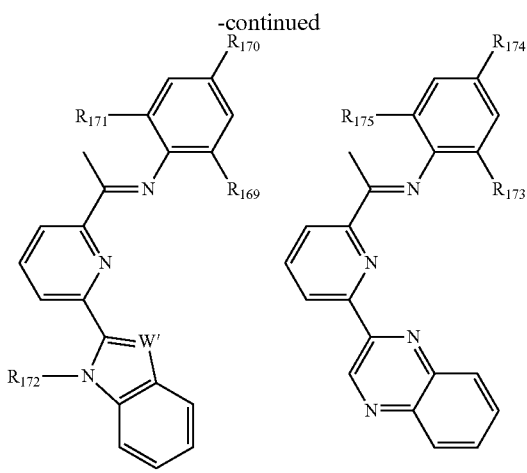

where the groups $R^1$ to $R^{193}$ is optionally identical or different, are hydrogen, a linear or branched alkyl group, which is optionally cyclic, saturated or unsaturated, an aryl, aralkyl or alkaryl group with 1 to 12 carbon atoms, a group containing a heteroelement, which is optionally heterocyclic, aromatic, halide, or substituted;
where $A^1$ to $A^6$ are carbon where n is a whole number of between 1 and 4, W is oxygen, sulfur or NH, W' is NH.

4. The catalytic composition according to claim 1, also comprising an additional activating agent that is a different alkylaluminum, a different alkylaluminum hydride, an aluminoxane, a trialkylboranes, an tris(aryl)borane, an (aryl)borate combined with a triphenyl carbenium or with a tri-substituted ammonium cation, or a dialkylzinc.

5. The catalytic composition according to claim 1, which is prepared in the presence of at least one solvent that is an ether, alcohol, chlorinated solvent, hydrocarbon that is saturated, unsaturated, aromatic, or, cyclic.

6. A process for oligomerization of olefins comprising 2 to 10 carbon atoms comprising subjecting said olefins to oligomerization conditions in the presence of a catalytic composition according to claim 1.

7. The process for oligomerization of olefins according to claim 6, in which the olefin is ethylene, propylene, butene-1 or pentene-1, by itself or in a mixture, in pure or dilute form.

8. The process for oligomerization of olefins according to claim 6, in which selective oligomerization is carried out at a temperature of between −40 to +250° C. and at a pressure that varies from atmospheric pressure at 20 MPa, with or without the presence of a solvent that is an ether, alcohol, chlorinated solvent, hydrocarbon, wherein the hydrocarbon is saturated, unsaturated, aromatic, or cyclic.

* * * * *